United States Patent
Makharinsky et al.

(10) Patent No.: US 11,045,653 B1
(45) Date of Patent: Jun. 29, 2021

(54) MULTI-ELECTRODE LEADS, ADAPTERS, AND METHODS FOR LEFT BUNDLE BRANCH PACING WITH DEPTH CONTROL

(71) Applicant: Eagle Point Medical LLC, City of Dover, DE (US)

(72) Inventors: Leonid Makharinsky, Bonassola (IT); Daniel Lev Makharinsky, Chalfont St Giles (GB); Andrei Leonidovich Starostin, Moscow (RU)

(73) Assignee: Eagle Point Medical LLC, City of Dover, DE (US)

( * ) Notice: Subject to any disclaimer, the term of this patent is extended or adjusted under 35 U.S.C. 154(b) by 0 days.

(21) Appl. No.: 17/173,535

(22) Filed: Feb. 11, 2021

(51) Int. Cl.
*A61N 1/08* (2006.01)
*A61N 1/05* (2006.01)
*A61N 1/368* (2006.01)

(52) U.S. Cl.
CPC ....... *A61N 1/36842* (2017.08); *A61N 1/0573* (2013.01); *A61N 2001/058* (2013.01); *A61N 2001/083* (2013.01)

(58) Field of Classification Search
CPC .............. A61N 1/38642; A61N 1/0573; A61N 2001/083; A61N 2001/058
See application file for complete search history.

(56) References Cited

U.S. PATENT DOCUMENTS

| | | | |
|---|---|---|---|
| 5,458,629 A | 10/1995 | Baudino | |
| 6,449,509 B1 * | 9/2002 | Park | A61N 1/36521 600/533 |
| 7,047,083 B2 | 5/2006 | Gunderson | |
| 7,200,441 B2 | 4/2007 | Prutchi | |
| 8,538,523 B2 | 9/2013 | Sommer | |
| 8,620,458 B1 * | 12/2013 | Sengupta | A61N 1/3702 607/127 |
| 8,996,126 B2 | 3/2015 | Stevenson | |
| 10,016,607 B2 | 7/2018 | Min | |
| 2008/0009927 A1 * | 1/2008 | Vilims | A61N 1/36071 607/115 |
| 2014/0214110 A1 | 7/2014 | Yang | |
| 2018/0078169 A1 | 3/2018 | Feldman | |
| 2018/0279897 A1 * | 10/2018 | Eddy | A61N 1/056 |
| 2019/0351219 A1 | 11/2019 | Mercanzini | |

(Continued)

OTHER PUBLICATIONS

H. Hughes Jr. et al. Failure of Demand Pacing with Small Surface Area Electrodes. Circulation, vol. 54, No. 1, pp. 128-132.

(Continued)

*Primary Examiner* — William J Levicky
(74) *Attorney, Agent, or Firm* — Boris Leschinsky (57) ABSTRACT

A method for pacing left bundle branch of the heart comprising implantation of a multi-electrode lead at a desired depth into the interventricular septum from the right ventricle, wherein the depth control during the implantation of the distal electrode is provided by monitoring electrical impedance for one or more intermediate electrodes. Reaching of exceeding a threshold of electrical impedance change is used to determine the entry of a corresponding intermediate electrode from the blood stream in the right ventricle into the cardiac tissue of the septum. Known distances between intermediate spaced apart electrodes and the distal electrode allow determination of the implantation depth of the distal electrode.

17 Claims, 9 Drawing Sheets

(56) References Cited

U.S. PATENT DOCUMENTS

2020/0069196 A1\* 3/2020 Hettrick ............... A61B 5/4848
2020/0390363 A1\* 12/2020 Addison .............. A61B 5/0538
2021/0015389 A1\* 1/2021 Zhou .................. A61N 1/36521

OTHER PUBLICATIONS

H Kalvoy et al. Impedance-based tissue discrimination for needle guidance. Physiol. Meas. 30 (2009), p. 129-140.
D C Deno et al. Measurement of Electrical Coupling Between Cardiac Ablation Catheters and Tissue. IEEE Trans Biomed Eng. vol. 61, No. 3, pp. 765-774. Mar. 2014.
D Schwartzman et al. Electrical Impedance Properties of Normal and Chronically Infarcted Left Ventricular Myocardium. J Int Card Electrophysiology 1999, 3; 213-224.
W Huang at al. A beginner's guide to permanent left bundle branch pacing. Heart Rhythm. Dec. 2019;16(12):1791-1796.
S Padala et al. Left bundle branch pacing is the best approach to physiological pacing. Perspectives in Contrast| vol. 1, Issue 1, p. 59-67, Apr. 1, 2020.

\* cited by examiner

MULTI-ELECTRODE LEADS, ADAPTERS, AND METHODS FOR LEFT BUNDLE BRANCH PACING WITH DEPTH CONTROL

BACKGROUND

Without limiting the scope of the invention, its background is described in connection with cardiac pacing. More particularly, the invention describes improved pacing leads, adapters for connecting to a conventional pacemaker and methods for left bundle branch (LBB) pacing with closely monitored depth control during electrode implantation.

Figure 1:
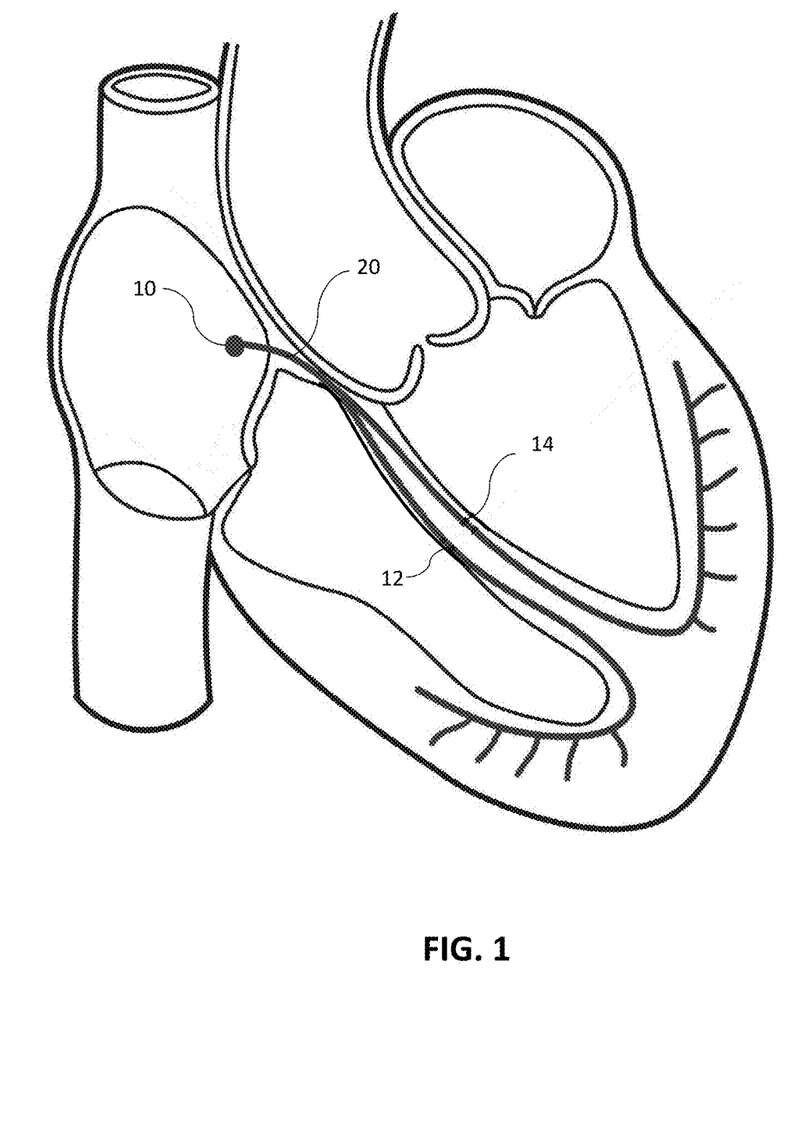
FIG. 1 is a general view of the hear showing His bundle bifurcating into a right bundle branch and a left bundle branch.

The last decade has seen a surge of conduction system pacing, especially for patients with symptomatic bradycardia and heart failure. His bundle pacing is now an accepted alternative to a more traditional ventricular pacing, typically conducted at the right ventricle apex/outflow tract or a coronary sinus. FIG. 1 illustrates a heart with the AV node shown as position 10, and His bundle fibers as position 20, which bifurcates into a right bundle branch 12 and a left bundle branch 14. Although His bundle pacing is conceptually attractive, it still has some inherent limitations. The implant technique for a conventional His bundle lead requires greater expertise in targeting a small electrode implantation zone in the heart, which may be especially challenging in patients with dilated hearts. The success of implantation as reported in the literature varies from 56% to 95% depending on the degree of conduction system disease and the experience of the center. My previous patent application Ser. No. 16/035,653 entitled "Single conduit multi-electrode cardiac pacemaker and methods of using same" and Ser. No. 16/293,104 with the same title illustrate some prior art attempts to reduce these clinical difficulties with advanced technology.

In addition to initial uncertainty of lead positioning during lead implantation, His bundle pacing is fraught with troubleshooting issues at follow-up. His bundle leads may have a low R-wave amplitude that may result in oversensing of atrial or His signals and under-sensing of ventricular signals. High His bundle capture thresholds at the time of implantation and/or during late follow-up may result in premature battery depletion and repeated pacemaker replacement, which are associated with additional clinical risks to the patient. The unpredictable, delayed rise of His bundle capture thresholds are of concern as well, resulting in higher lead revision rates.

A quest for a better pacing site led to a novel conduction system pacing technique, first described in 2017, where the pacing lead was implanted deep into the right ventricle basal septum to capture the left bundle branch area of the heart. This technique is especially beneficial in patients with demonstrated left bundle branch block as His bundle pacing may not be appropriate to assist with this condition. LBB pacing is rapidly emerging as an attractive alternative to the failed His bundle pacing and even as a primary pacing strategy in a variety of patients. Both anatomy (narrow target for His bundle pacing vs. wide target for LBB pacing) and tissue structure (His bundle is encapsulated in fibrous, electrically non-conductive tissue vs. LBB embedded in myocardium) favor LBB over His bundle for a more physiological pacing.

Figure 2:
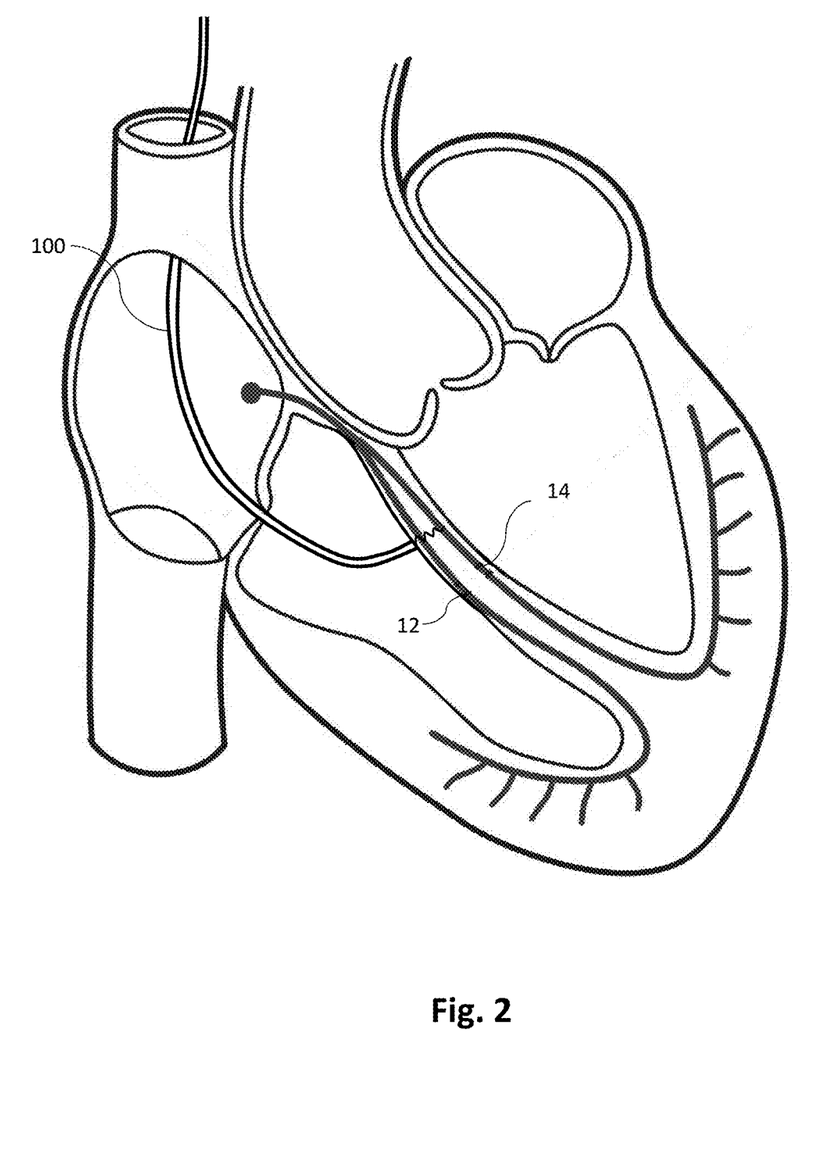
FIG. 2 shows a general position of a pacing electrode inside the right ventricle with the distal portion engaged with the interventricular septum.
Figure 3:
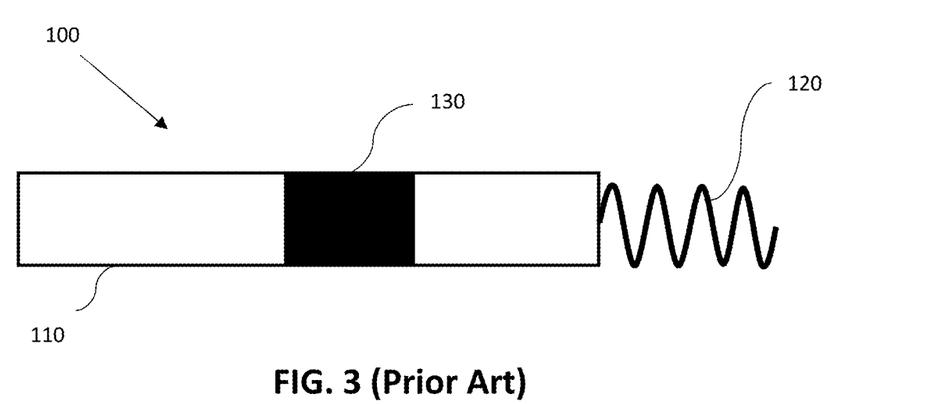
FIG. 3 is a side view of a distal portion of a prior art pacing lead.

LBB pacing is typically performed with a bipolar lead 100 deployed into the interventricular septum from the right ventricle—as shown in FIG. 2. One example of a suitable lead is a SelectSecure 3830 pacing lead manufactured by Medtronic, Minneapolis, Minn., and delivered using a fixed curve C315-HIS sheath or the newer SelectSite C304-HIS deflectable sheath, produced by the same company. Conceptually, a distal portion 110 of such bipolar lead 100 is shown in FIG. 3 and includes a distal screw electrode 120 configured to engage with the cardiac tissue upon rotation, and a spaced apart electrode 130. A proximal portion of the lead 100 (not shown) may have a conventional two-electrode connector configured for secure attachment to a conventional pacemaker.

Although LBB pacing is gaining in popularity, deployment of the electrode into an interventricular septum is not without difficulties. Variations in patient's anatomy may account for certain differences in interventricular thickness, which may vary from about 10 mm to about 20 mm. In addition to uncertain overall septum thickness, the location of LBB conductive fibers deep inside the septal tissue is also variable between patients, typically located closer to the left ventricle border of the septum, such as about 1-5 mm therefrom. To assure successful left ventricle capture at the lowest capture threshold, the distal electrode of the lead may need to be deployed as close to the LBB fibers as possible, while avoiding the risk of penetrating through the septum and entering the left ventricular cavity.

The need exists therefore for a pacing lead and LBB pacing methods that assures lead deployment into the interventricular septum with accurate depth control—in order to (i) achieve left ventricle capture at the lowest effective voltage, and at the same time (ii) avoid puncturing through the septum.

SUMMARY

Accordingly, it is an object of the present invention to overcome these and other drawbacks of the prior art by providing a novel multi-electrode lead configured to allow for depth control during its implantation into cardiac tissue.

It is another object of the present invention to provide a novel multi-electrode lead configured for implantation at a predetermined depth in the cardiac tissue.

It is a further object of the present invention to provide a novel multi-electrode lead and methods of implantation and use configured for pacing of the left bundle branch of the heart.

It is yet a further object of the present invention to provide a novel adapter configured to allow use of conventional pacemaker for pacing the heart using a multi-electrode lead of the present invention.

The novel multi-electrode lead may include a first distal fixation electrode, which may be made as a screw configured to secure the electrode inside cardiac tissue. A second pacing electrode may be positioned proximally from the first distal electrode along the lead at a predetermined distance therefrom. At least one or a plurality of spaced apart intermediate electrodes may be positioned between the first electrode and the second electrode, at predetermined locations on the insulated elongated flexible body of the lead.

Electrical impedance may be continuously or intermittently monitored for at least one, several, or all the intermediate electrodes during the lead implantation procedure. Additional impedance detection may be provided for the first electrode and/or the second electrode at the same time. A change of impedance for each of the monitored electrodes reaching or exceeding a predefined impedance change threshold may be used to detect the point of contact and entry of the monitored electrode into the cardiac tissue. Knowing the position of each electrode relative to other electrodes and relative to the first electrode allows determination of the depth of penetration of the first electrode into the cardiac tissue.

Impedance monitoring may be conducted using a specialized cardiac monitor and pacing controller configured for operating some or all electrodes of the multi-electrode lead. Once the position of the lead inside the cardiac tissue is optimized, a conventional cardiac pacemaker may be connected to the proximal portion of the multi-electrode lead using an adapter configured to provide pacing stimulation to the heart using the selected electrodes of the multi-electrode lead. Other electrodes may be either abandoned or coupled together with the selected electrodes to increase the surface area available for pacing and reduce the capture threshold.

Impedance monitoring may be conducted either in a unipolar fashion (between the respective electrode and a ground electrode) or in a bipolar fashion, where impedance between one or more designated pair of electrodes may be monitored, for example between the first distal electrode and at least one or more intermediate electrodes, or between a pair of intermediate electrodes. More than one pair of electrodes may be monitored for their respective impedance at the same time.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

First Embodiment of the Present Invention

Figure 4:
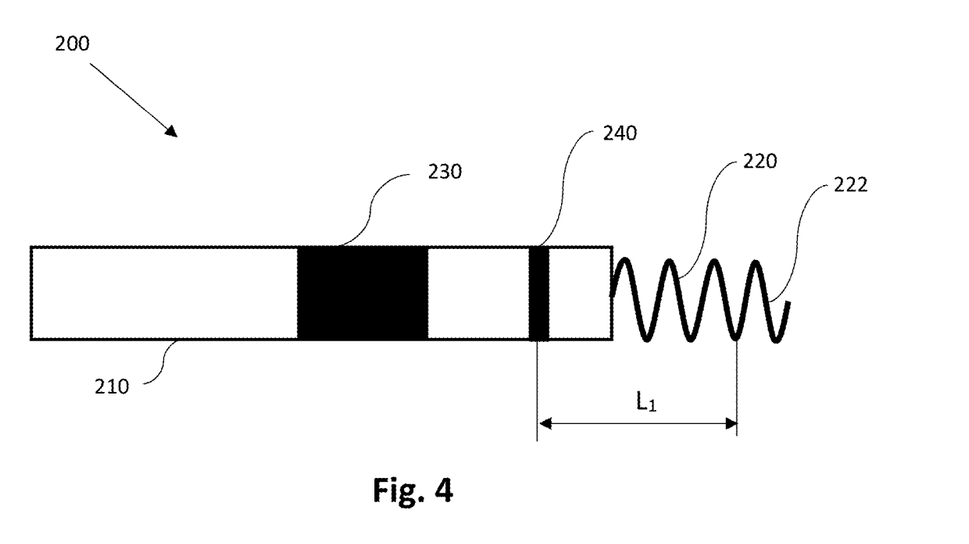
FIG. 4 is a side view of a distal portion of the first embodiment of the present invention.

FIG. 4 illustrates a distal portion 210 of the multi-electrode lead 200 according to the first embodiment of the present invention. The lead 200 may comprise a generally insulated elongated flexible body with a first electrode 220 protruding distally from its distal portion 210. The first electrode 220 may be made with a tissue fixation feature, for example as a screw. In other embodiments, other than a screw features may also be used, for example barbs, hooks, etc. as the invention is not limited in this regard.

Referring back to FIG. 4, the first electrode 220 may have a tip 222 electrically exposed to the cardiac tissue to provide electrical contact therewith, while the remaining portion of the screw 220 may optionally be insulated, for example by using a non-conductive coating. In other embodiments, a larger portion of or even the entire screw 220 may be exposed to cardiac tissue, as the invention is not limited in this regard. The length of the first electrode may vary from about 1.5 mm to about 8 mm and may be about 1.5 mm, about 3 mm, about 4 mm, about 5 mm, about 6 mm, about 7 mm, about 8 mm, or any length inbetween. The first electrode 220 may be made from a suitable metal with sufficient electrical conductivity. It may optionally be coated using known cardiac electrode coatings, for example a steroid coating for improved healing. The first electrode 220 may be typically used as a cathode during cardiac pacing. A first dedicated electrical conductor may be provided to electrically couple the first electrode 220 at the distal portion 210 with a corresponding first connector electrode at the proximal end of the multi-electrode lead 200, with this first conductor located inside the generally insulated elongated body of the lead 200 (not shown in FIG. 4).

A second optional electrode 230 may be provided along the distal portion 210 of the multi-electrode 200 and may be proximally spaced apart from the first electrode by a distance that may range from about 3 mm to about 15 mm. The present invention may be operated without the second electrode, such as in a unipolar mode of cardiac pacing. However, to utilize a more acceptable bipolar mode of cardiac pacing, the second electrode 230 may be provided and used as explained in greater detail below.

In embodiments, the distance between the first electrode and the second electrode along the elongated body of the lead may be about 3 mm, 5 mm, 7 mm, 9 mm, 11 mm, 13 mm, 15 mm or any length inbetween. The second electrode 230 may be made as a ring with a width ranging from about 1 mm to about 6 mm, for example 1 mm, 2 mm, 3 mm, 4 mm, 5 mm, 6 mm, or any width inbetween. The ring electrode 230 may be electrically exposed to cardiac tissue and may be coated in a manner similar to the first electrode 220. The second electrode 230 may be used as an anode during cardiac pacing. A second dedicated electrical conductor may be provided to electrically couple the second electrode 230 at the distal portion 210 with a corresponding second connector electrode at the proximal end of the multi-electrode lead 200, with this second conductor located inside the generally insulated body of the lead 200 (not shown in FIG. 4).

The multi-electrode lead 200 of the first embodiment of the invention may further feature an intermediate electrode 240 located on the distal portion 210 between the first electrode 220 and the second electrode 230. In one non-limiting example, such intermediate electrode may be a ring electrode made in a manner similar to the second electrode 230. The width of the intermediate electrode 240 may be about 0.5 mm to 4 mm, such as 0.5 mm, 1 mm, 2 mm, 3 mm, 4 mm, or any width inbetween. The intermediate electrode 240 may be located at a predetermined distance Li from the tip 222 of the first electrode 220. The distance Li may be selected to correspond to the desired depth of penetration of the first electrode 220 into cardiac tissue during implantation thereof as explained in greater detail below. In embodiments, the distance Li may be selected to be from 8 mm to 18 mm, such as 8 mm, 10 mm, 12 mm, 14 mm, 16 mm, 18 mm, or any distance inbetween. An intermediate dedicated electrical conductor may be provided to electrically couple the intermediate electrode 240 at the distal portion 210 with a corresponding intermediate connector electrode at the proximal end of the multi-electrode lead 200, with this intermediate conductor located inside the generally insulated body of the lead 200 (not shown in FIG. 4).

The multi-electrode lead 200 of the first embodiment of the invention may be used advantageously to deploy the first electrode 220 at a predetermined depth into cardiac tissue using impedance measurements of at least the intermediate electrode 240 during the implantation procedure. There is a measurable reduction in electrical impedance for a particular electrode when the electrode is advanced from a location in a blood stream to a location at or inside the cardiac tissue. Electrical impedance may be measured between the intermediate electrode 240 and a ground electrode. Alternatively, electrical impedance may be measured between the intermediate electrode 240 and the first electrode 220.

Impedance measurements may be obtained using various measurement parameters. Frequency of test impulses is one of these parameters characterizing the impedance measurement process. In embodiments, a preferred frequency of impedance impulse generation may be selected between a predetermined value and the value that may be obtained by testing at the beginning of the implantation procedure. Various frequencies may provide different sensitivity to the impedance change when a particular electrode enters into the cardiac tissue, so that such initial test may be instrumental in determination of the testing frequency showing maximum sensitivity of the impedance measurements to contact with cardiac tissue—which will assure most accurate depth measurements of the first distal electrode 220.

Monitoring of electrical impedance of the intermediate electrode 240 during implantation of the lead 200 in the heart allows detection of a moment when the electrical impedance change exceeds a predetermined impedance change threshold, which indicates the moment of contact and entry of the intermediate electrode 240 into cardiac tissue. Once such impedance change is detected to exceed this threshold, further advancement of the first electrode 220 may be ceased and the location of the first electrode 220 may be assumed to be at a desired distance Li from the cardiac tissue entry point.

Figure 10A:
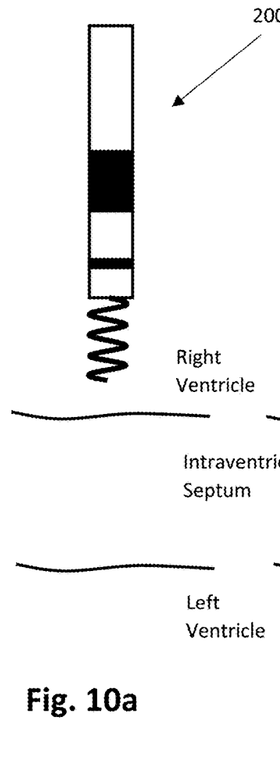
FIGS. 10a through 10d illustrate stages of deployment of the multi-electrode lead of the present invention.
Figure 10B:
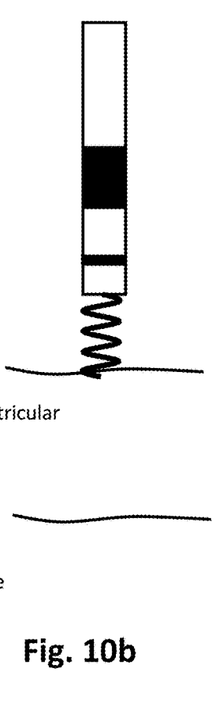
Figure 10C:
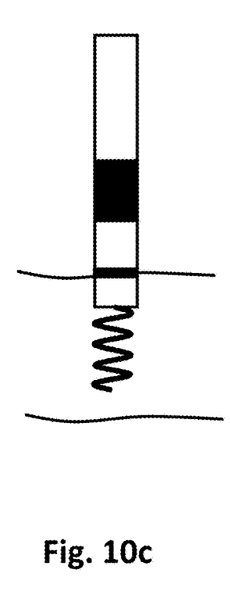

According to one method of the invention, a left bundle branch or another desired location of the heart may be paced using the following steps of implantation and operation:

a. providing a multi-electrode lead 200 according to the first embodiment of the invention with the distance Li between the first electrode 220 and the intermediate electrode 240 selected to correspond to the desired depth of implantation of the first electrode 220;

b. positioning the distal portion 210 of the multi-electrode lead 200 in the right ventricle of the heart adjacent to a desired location of implantation at the interventricular septum of the heart—see FIG. 10a;

c. intermittently or continuously monitoring electrical impedance of at least the intermediate electrode 240;

d. detecting the baseline electrical impedance thereof while located in a blood stream inside the right ventricle of the heart;

e. initiating deployment of the first distal electrode 220 into cardiac tissue of the interventricular septum—see FIG. 10b;

f. upon detection of a change in electrical impedance of the intermediate electrode 240 at or exceeding a predetermined electrical impedance change threshold, ceasing further deployment of the first electrode 220 as reaching the desired implantation depth—see FIG. 10c; and g. initiating a unipolar or bipolar pacing of the heart using the first electrode 220 and the second electrode 230.

The electrical impedance change threshold may have a predetermined value in absolute or relative units of electrical impedance. For example, such value for impedance change threshold may be selected at 25 Ohm, 50 Ohm, 75 Ohm, 100 Ohm, 150 Ohm, 200 Ohm, or any value inbetween—as a difference between the electrical impedance measurement when the intermediate electrode 240 is in cardiac tissue compared to the baseline measurement of impedance when the intermediate electrode 240 is located in the blood stream. In other embodiments, the threshold of the change in impedance value may be selected to be 10%, 15%, 20%, 25%, 30%, 35%, 40%, or any value inbetween, with the percent change applied to the initial baseline measurement of electrical impedance when the intermediate electrode 240 is known to be in the blood stream.

To eliminate the impact of the timing of cardiac contractions and movement on impedance measurements, in some embodiments, impedance measurements may be synchronized to the heart rhythm—in other words, impedance measurements may be made during the same phase of the cardiac cycle throughout the implantation procedure.

Electrical impedance may be measured between a selected electrode and a ground electrode. In other embodiments, electrical impedance may be measured between a pair of electrodes, for example between the first electrode 220 and the intermediate electrode 250. In case of measuring the impedance in a bipolar way between adjacent electrodes, the baseline measurement in blood may show an increase when encountering cardiac tissue as electrical resistance inside the tissue may be greater than that of the blood stream. On the other hand, unipolar impedance measurement may first show a decrease when the electrode enters the cardiac tissue. Such decrease may persist and then show an increase when the electrode may approach the other side of the interventricular septum.

Because of these considerations, the present invention relies on a notion of impedance change as compared with a predetermined impedance change threshold as an indication of an electrode coming in contact with cardiac tissue, regardless of whether the absolute value of the impedance goes up or down.

Several additional steps of the method may be used to further enhance the accuracy of deployment and verify the first electrode 220 reaching the desired position and depth of deployment. One of these steps may include monitoring of electrical impedance of the first electrode 220 and/or the second electrode 230. With regard to the impedance of the first electrode 220, initial values upon entry into cardiac tissue may show a decline in electrical impedance as the first electrode 220 is implanted deeper into the tissue. At some point, however, the impedance of the first electrode 220 may show an increase as it gets closer to the boundary of the interventricular septum with the left ventricle—see FIG. 10d. Monitoring the impedance of the first electrode 220 may be used as a secondary measure to avoid an inadvertent penetration of the first electrode into left ventricular cavity, for example by ceasing its implantation procedure once an increase of electrical impedance thereof is detected.

Monitoring of the electrical impedance of the second electrode 230 may also be performed as a safety assurance step. Detecting of a rapid change in impedance of the second electrode 230 may indicate a close contact or even a partial penetration of the second electrode 230 into cardiac tissue, in which case the implantation procedure may be stopped or even partially reversed.

Furthermore, the intermediate electrode 240 may not only be monitored for electrical impedance, but also it may be intermittently tried for capture of the right ventricle. Once the intermediate electrode 240 is detected to enter the cardiac tissue by the change in electrical impedance reaching or exceeding a predetermined impedance change threshold, it may be confirmed by detecting the ability thereof to capture the right ventricle, indicating its location near the right bundle branch of the conduction fiber system.

Once the implantation procedure is complete, further use of the intermediate electrode 240 may be abandoned. In other embodiments, the intermediate electrode may be electrically coupled with the first distal electrode and used as a joint cathode, if that is found to be advantageous for reducing the capture threshold during cardiac pacing. In further yet embodiments, the intermediate electrode 240 may be elected to serve in place of the first distal electrode 222 at some future point—in case of a detected malfunction thereof.

Second Embodiment of the Present Invention

Figure 5:
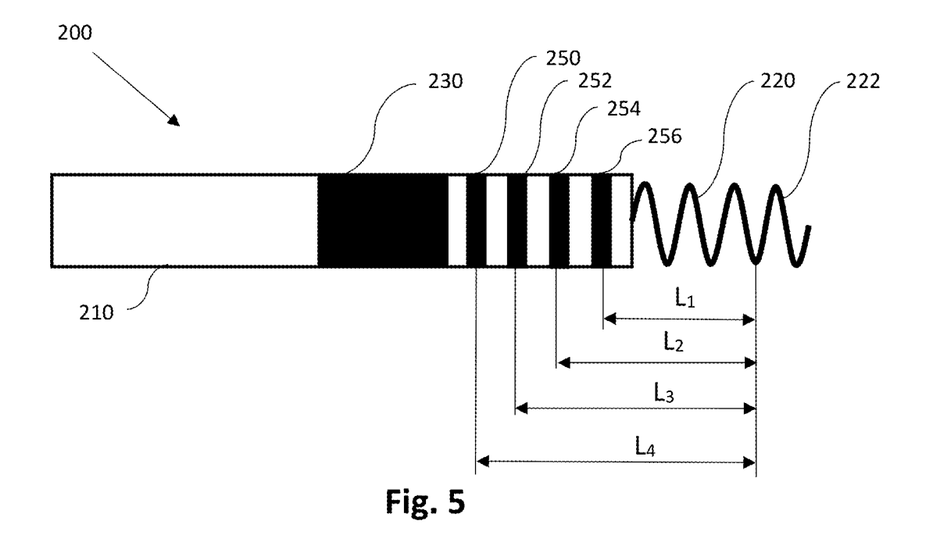
FIG. 5 is a side view of a distal portion of the second embodiment of the present invention.

The distal portion 210 of the multi-electrode lead 200 according to the second embodiment of the invention is seen in FIG. 5. Similarly to the first embodiment, it features a first distal electrode 220 with a tip 222 electrically exposed to cardiac tissue and a second electrode 230 proximally spaced apart from the first distal electrode 222. As compared to the first embodiment, more than a one intermediate electrode 205, 252, 254, and 256 form together a plurality of intermediate electrodes located inbetween the first electrode 220 and the second electrode 230. In embodiments, the plurality of intermediate electrodes may include 2, 3, 4 (as shown in FIG. 5), 5, 6, 7, 8 or more electrodes as the invention is not limited in this regard. Each intermediate electrode of the plurality of intermediate electrodes may be spaced apart from adjacent intermediate electrodes by the same distance as other electrodes or by variable distances. The distance between adjacent intermediate electrodes may be from about 1 mm to about 3 mm and may include 1 mm, 1.5 mm, 2 mm, 2.5 mm, 3 mm or any distance inbetween. These distances may be measured from the center of each respective intermediate electrode.

A plurality of intermediate dedicated electrical conductors may be provided to electrically couple the intermediate electrodes 250-256 at the distal portion 210 with a corresponding plurality of intermediate connector electrodes at the proximal end of the multi-electrode lead 200, with intermediate conductors located inside the generally insulated body of the lead 200 (not shown in FIG. 5).

Intermediate electrodes 250-256 may be used to more accurately detect the depth of implantation of the tip 222 of the first distal electrode 222 into the cardiac tissue. Knowing the distances $L_1$ through $L_4$ in the example of FIG. 5 that correspond to the locations of intermediate electrodes 250-256 away from the tip 222 allows detection of the depth of penetration of the first electrode 222 into the heart tissue as described below.

As explained above, the thickness of the interventricular septum may vary from one patient to the next. With this uncertainty, the first embodiment of the invention allowing deployment at a fixed depth may have a limitation of being useful only for certain size patients. The second embodiment of the invention is therefore more universally applicable to a broader range of patients as it allows to accommodate various desired depths depending on the individual anatomy of the patient.

According to the methods of using the second embodiment of the invention to implant the multi-electrode lead for stimulation of the left bundle branch of the heart at a desired depth of electrode penetration, the steps of implantation and operation of the multi-electrode lead may be as follows:

a. providing a multi-electrode lead 200 according to the second embodiment of the invention with known distances between the first electrode 220 and the plurality of intermediate electrodes 250-256;

b. selecting a desired depth of implantation of the first electrode 222 into the interventricular septum of the heart;

c. positioning the distal portion 210 of the multi-electrode lead 200 in the right ventricle of the heart adjacent to a desired location of implantation, such as in one example at the interventricular septum of the heart;

d. intermittently or continuously monitoring electrical impedance of the individual intermediate electrodes 250-256 of the plurality of intermediate electrodes;

e. detecting the baseline electrical impedance for at least one or more of the intermediate electrodes 250-256 while located in a blood stream inside the right ventricle of the heart;

f. initiating deployment of the first distal electrode 220 into cardiac tissue of the interventricular septum;

g. detecting changes in electrical impedance for successive intermediate electrodes at or exceeding a predetermined electrical impedance change threshold, indicating penetration thereof into cardiac tissue;

h. ceasing further deployment of the first electrode 220 at the desired implantation depth once cardiac tissue contact or penetration of the intermediate electrode corresponding to the desired depth of implantation is detected; and i. initiating a bipolar pacing operation of the multi-electrode lead 200 using the first electrode 220 and the second electrode 230.

Similarly to what is described for the first embodiment of the invention, the electrical impedance change threshold may be determined for each individual intermediate electrode 250-256 or designated as a single impedance change threshold for all of the intermediate electrodes, especially in case they are all made to have the same design. An absolute measure of impedance deviation in Ohms or a relative measure of deviation of impedance in percent of baseline may be used to detect the contact and/or penetration of each of the individual intermediate electrodes into the cardiac tissue.

Another advantage of the second embodiment of the invention as compared to the first embodiment is the ability to make multiple impedance measurements at the same time. Having such multiple measurements may help to isolate and ignore occasional artifact measurements as it can be assumed that all intermediate electrodes would show electrical impedance measurements of the same order of magnitude.

In addition, once the deployment of the first electrode is complete, one, several or all of the intermediate electrodes may be connected together and with the first distal electrode for the purpose of increasing the contact area of the combined pacing electrode. In other embodiments, one, several or all of the intermediate electrodes may be abandoned or used for future purposes of heart assessment of as back-up pacing electrodes in case of detecting any failure of original pacing electrodes.

Third Embodiment of the Invention

Figure 6:
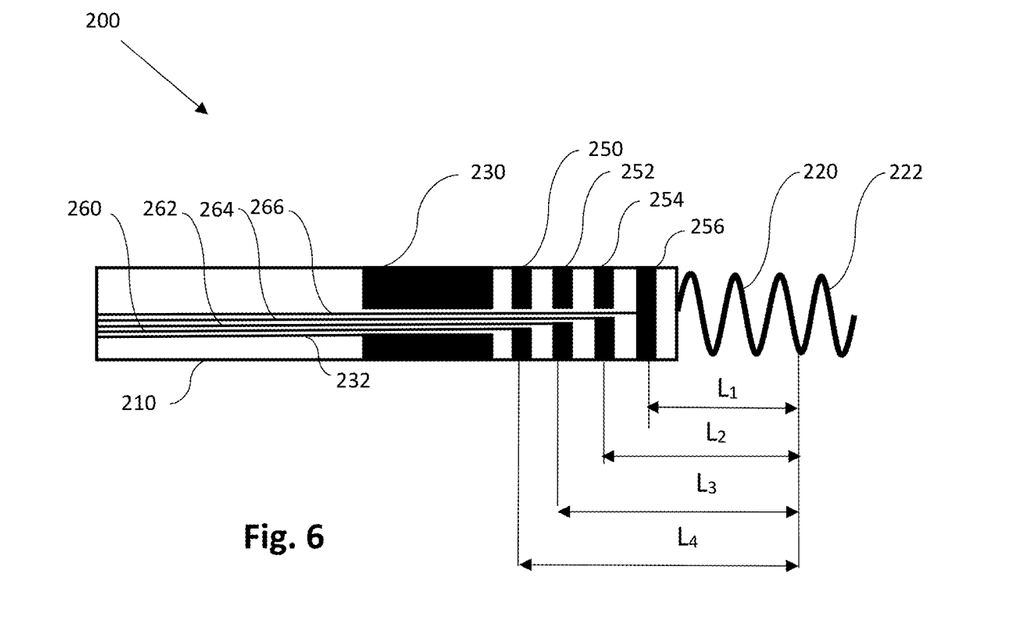
FIG. 6 is a side view of a distal portion of the third embodiment of the present invention.

FIG. 6 illustrates a distal portion 210 of the multi-electrode lead 200 of the third embodiment of the present invention. In this case, a plurality of conductors connecting the distal electrodes with the proximal connectors may be located on an external surface of the insulated body of the lead 200. FIG. 6 shows an example of a conductor 266 connected to the intermediate electrode 256, which may still be made a ring. Adjacent intermediate electrode 254 may be equipped with a conductor 264. The individual electrode 254 may be made as a C-shaped arch rather than a full ring. The arch may cover almost all of the circumference of the lead 280 but leave room for running the conductor 266 therethrough. The next individual electrode 252 may also be made as a C-shaped arch with an opening sufficient to run individual conductors 264 and 266 to respective individual electrodes 254 and 256, while the electrode 252 may be connected to a respective individual conductor 262. The same may be done for the pairs of electrodes/conductors 250/260 and, finally, 230/232.

Once individual conductors are located along the external surface of the multi-electrode lead 200, an electrically insulating coating may be applied to prevent them from being exposed to blood or cardiac tissue and avoid shorting the circuits.

The use of the third embodiment of the invention may be the same as that for the second embodiment described in greater detail above.

Fourth Embodiment of the Invention

Figure 7:
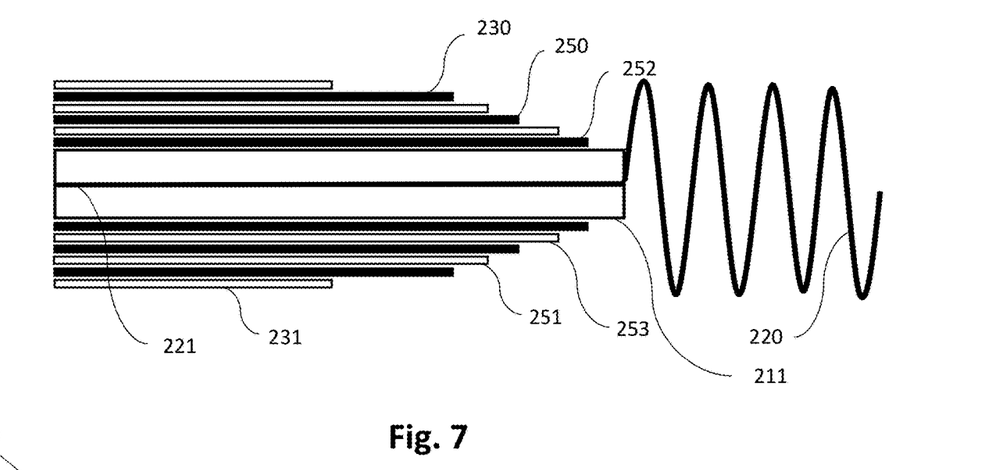
FIG. 7 is a side view of a distal portion of the fourth embodiment of the present invention.

FIG. 7 shows a distal portion of the multi-electrode lead according to the fourth embodiment of the present invention. A generally insulated elongated flexible body 211 may contain a first distal electrode 220, which may be connected electrically with the proximal portion of the lead via an internal conductor 221. A series of layers 252, 253, 250, 251, 230, 231, may be concentrically applied over the general insulated body 211. These concentric layers may be arranged in an alternating pattern, with conductive metallic layers 252, 250, 230 alternating with non-conductive layers 253, 251, 231. This arrangement may further be designed to electrically expose the distal tips of every conductive layer so as to form the second electrode 230 as well as at least one or a plurality of intermediate electrodes, such as two electrodes 250 and 252 as seen in FIG. 7. The outer diameter of the external non-conductive layer 231 may be selected to not exceed the diameter of the tissue fixation screw of the first electrode 220. Each conductive concentric layer may be extended towards the proximal end or feature a dedicated conductor that connects thereof to the proximal connector electrodes of the multi-electrode lead 200. Each layer may have a minimal thickness so that a combination of these layers does not increase the overall diameter of the lead 200.

During the implantation procedure, it is expected that the exposed tips of each conductive layer may act as independent intermediate electrodes in a manner that is similar to that described for previous embodiments of the device, and therefore may present an alternative design configuration for the purposes of the present invention.

Fifth Embodiment of the Invention

Figure 8:
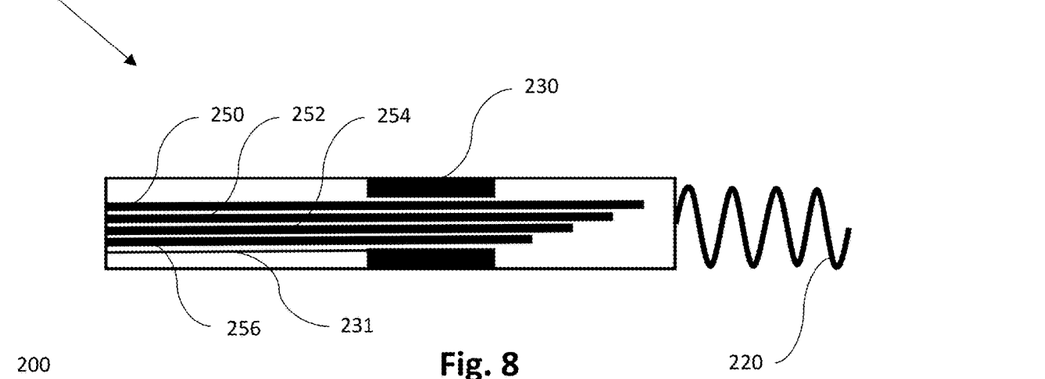
FIG. 8 is a side view of a distal portion of the fifth embodiment of the present invention.

Alternative arrangement of intermediate electrodes 250-256 is shown in FIG. 8 as the fifth embodiment of the multi-electrode lead 200 of the present invention. The lead 200 may feature a first distal electrode 220 and a second electrode 230 proximally spaced apart from the first electrode 220 and connected to the proximal connector electrode (not shown) of the lead by a conductor 231. A plurality of parallel conductive strips 250, 252, 254, 256 may be arranged along the main body of the lead 200 to form these intermediate electrodes. These strips may be painted onto the main body of the lead 200, or alternatively affixed by gluing, electrical plating deposition, or by another suitable technique. The width of the conductive strips may range from about 0.5 to 3 mm, such as 0.5, 1, 1.5, 2, 2.5, 3 mm or any suitable width inbetween. All strips may have the same width, or in other embodiments, some strips may be wider than others. Only the distal tips of the strips 250-256 may be electrically exposed to the surrounding space, as the strips may be covered by an insulating coating. The length of the exposed tips may be about 1-4 mm, such as 1 mm, 2 mm, 3 mm, 4 mm, or any length inbetween as the invention is not limited in this regard. The tips of individual electrodes may be staggered along the length of the lead 200 and be all located between the first electrode 220 and the second electrode 230 as seen in the drawing.

During the implantation procedure of the lead 200, individual electrical impedance measurements of the tips of the strips 250-256 may be monitored and used as described above for detecting the depth of implantation of the first electrode 220 into cardiac tissue of the interventricular septum—in particular, from knowing the spatial relationship of these tips relative to the first distal electrode 220.

Sixth Embodiment of the Invention

Figure 9:
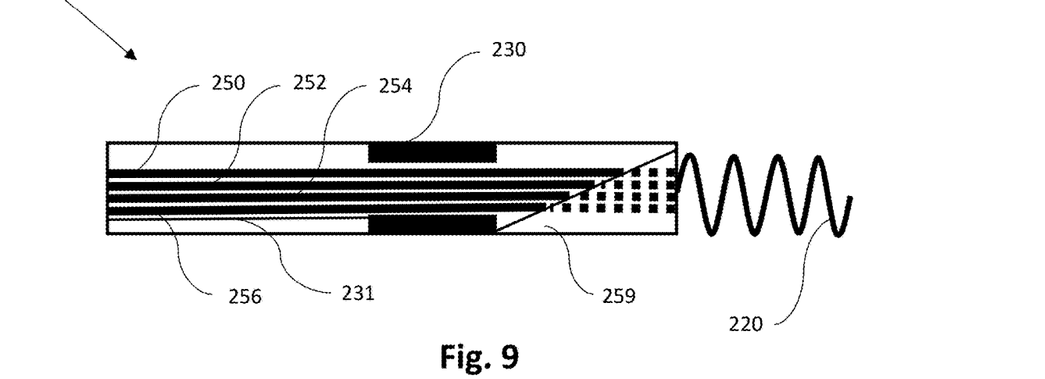
FIG. 9 is a side view of a distal portion of the sixth embodiment of the present invention.

A further variation of the fifth embodiment of the multi-electrode lead 200 is seen in FIG. 9. In this embodiment, all conductive strips 250-256 are made to extend all the way to the distal end of the elongated flexible body of the lead 200. To form a spaced apart staggered arrangement of the intermediate electrodes, a temporary coating 259 may be applied in an angular pattern as seen in the drawing—to assure that each strip is exposed to a surrounding space at a location which is longitudinally spaced apart from adjacent strips. The coating 259 may be made to dissolve once in contact with blood or cardiac tissue, for example in a matter of minutes to hours following the implantation of the lead 200.

During implantation of the lead 200, the coating 259 may help to use the tips of the strips 250-256 as intermediate electrodes as described in greater detail above. Following implantation and dissolution of the coating 259, the entire distal length of each strip 250-256 will become electrically exposed to the cardiac tissue. Connecting one, several or all of the strips 250-256 together and with the first electrode 220 may help to increase the contact surface area of the lead 200 within cardiac tissue and reduce the capture threshold of the pacing procedure, which in turn may be helpful in extending the battery life of the implantable pacemaker.

FIGS. 10a through 10d show various stages of implantation of the lead 200 according to any of the first through sixth embodiments of the present invention. Shown in FIG. 10a is a stage of implantation when the lead 200 is positioned in the right ventricle next to the target implantation area of the interventricular septum. Baseline impedance of at least the intermediate electrode or a plurality of individual measurements of electrical impedance values for each of the plurality of the intermediate electrodes may be taken.

Figure 10D:
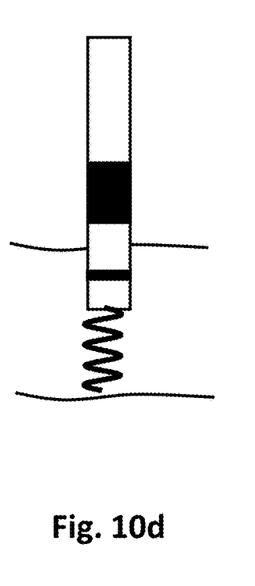

The electrode 200 may then be advanced to be in contact with the tissue (FIG. 10b) as can be confirmed by a changing electrical impedance of the first distal electrode reaching or exceeding a predetermined impedance change threshold. Further implantation of the first electrode may be monitored by a further reduction in its electrical impedance. Once a target depth of implantation is reached, the change in impedance of the intermediate electrode may be used to confirm the proper position of the first electrode—FIG. 10c. Implanting the first electrode deeper that desired may be detected by a changing impedance of the intermediate electrode as well as by an increase in the impedance of the first electrode, indicating its close proximity to the left ventricular cavity—as seen in FIG. 10d.

Seventh Embodiment of the Invention

Figure 11:
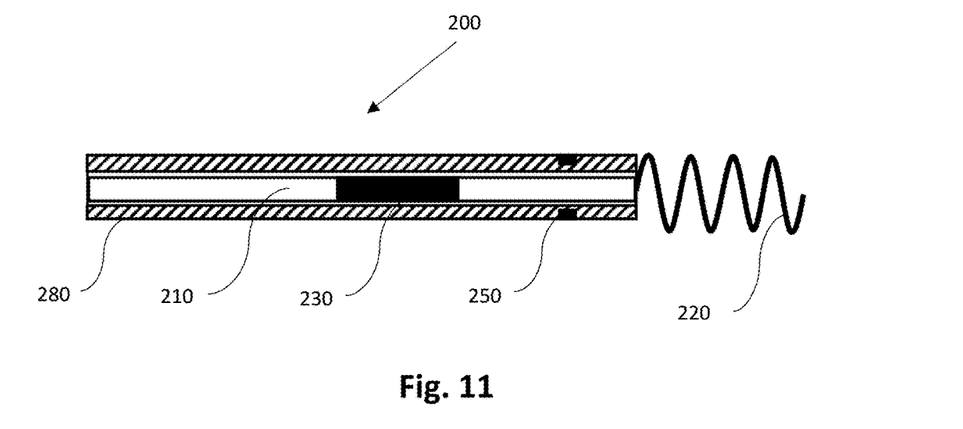
FIG. 11 is a side view of a distal portion of the seventh embodiment of the present invention.
Figure 12A:
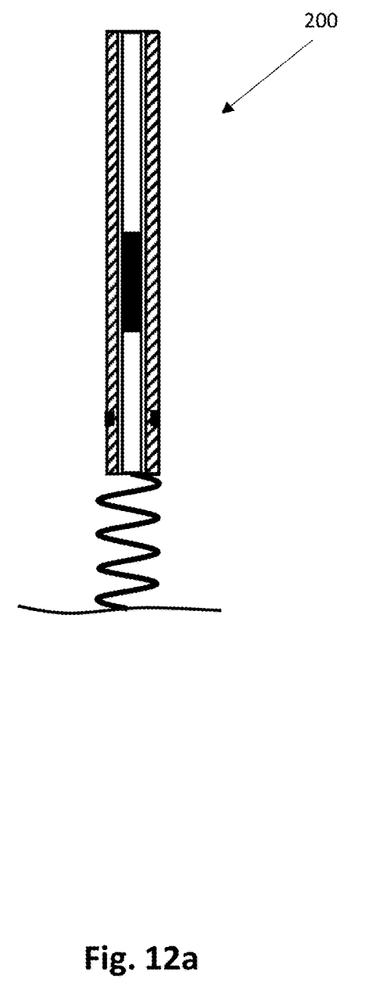
FIGS. 12a through 12c illustrate stages of deployment of the seventh embodiment of the invention.
Figure 12B:
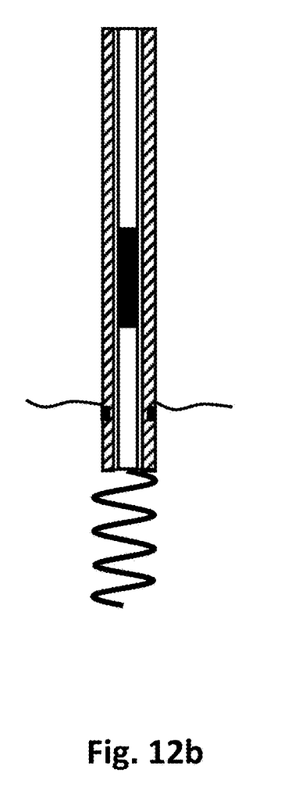
Figure 12C:
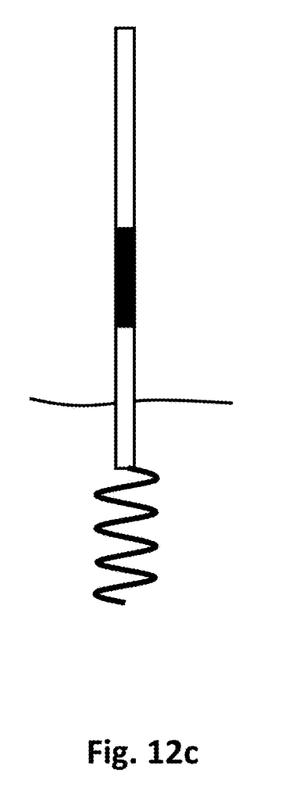

A distal portion of yet another, seventh embodiment of the invention is shown in FIG. 11 and its implantation steps are illustrated in FIGS. 12a through 12c. The purpose of this embodiment is to remove the intermediate electrodes after the implantation of the lead 200 is complete.

To accomplish this, the lead 200 generally comprises a lead body 210 equipped with a first distal electrode 220 and a second electrode 230—with appropriate internal electrical conductors to transmit the electrical signal between the proximal portion and the distal portion of the lead 200 (not shown). A thin external removable sheath 280 may be temporarily attached over the lead body 210, for example by using a proximally located reversible clamp (not shown). One or a plurality of intermediate electrodes 250 may be located at a location close to the first electrode 220 and spaced apart therefrom longitudinally along the central axis of the lead 200. The one or more intermediate electrodes 250 may be powered up via internal connectors embedded within the removable sheath 280 (not shown).

While in some embodiments, as shown in FIG. 11, the presence of the sheath 280 over the body 210 may conceal the second electrode 230 and prevent it from having an electrical contact with blood during implantation, in other embodiments, the sheath 280 may have a window cut-out located adjacent the location of the second electrode 230 when the sheath 280 is assembled with the lead body 210. Such window may expose the second electrode to blood and therefore provide for an opportunity to use it as an active electrode during the implantation procedure.

The number of intermediate electrodes, their respective position on the sheath 280, as well as the spatial relationship thereof between themselves and with the first electrode 220 may follow the description for the previous embodiments of the multi-electrode lead of the present invention as discussed above in greater detail.

Prior to implantation, the removable sheath 280 may be assembled over the lead body 210 so that the entire assembly may be implanted as a single unit—see FIG. 12a. During implantation, one or more intermediate electrodes 250 may be used to monitor their respective impedance indicating the depth of implantation of the first distal electrode 220, which may be advanced into the cardiac tissue of the interventricular septum by turning or by other commonly used advancement actions—see FIG. 12b.

Once the desired depth of implantation of the first electrode 220 is achieved, the removable sheath 280 may be untied from the lead body 210 and thereafter removed, leaving only the lead body 210, along with the first electrode 220 implanted at a desired location and depth and the second electrode 230 located at a desired position slightly above the tissue. Routine cardiac pacing of the LBB may then be commenced.

The seventh embodiment of the invention may be provided as a three-part system: (i) the main lead body 210, surrounded by (ii) the removable sheath 280 equipped with one or more intermediate electrodes 250, and (iii) a conventional curved outer sheath or a sheath with actively changing curvature. The implantation procedure in this case may follow a convention, wherein the outer sheath may be used to deploy a combination of the first two components as a single unit.

In further variations of the seventh embodiment, only two components may be needed to deliver the lead body 210, with the sheath 280 configured for both the delivery of the lead 200 as well as for assessment of the depth of penetration of the first electrode 220 into the cardiac tissue. To achieve this purpose, a desired curvature may be imparted into the sheath 280 to make it suitable for implantation of the first electrode 220 into the interventricular septum of the heart through a pathway leading into the right ventricle.

There are two advantages of the seventh embodiment of the invention as compared to the previous embodiments:

a. removal of the sheath 280 along with one or more intermediate electrodes 250 reduces the overall bulk of the remaining lead, reduces the restriction to surrounding venous blood flow, increases its flexibility, and reduces the risk of fatigue failure as a thinner lead body 210 may be less prone to fractures over time; and b. absence of additional intermediate electrodes 250 allows for a straight connection of the remaining first electrode and the second electrode to a conventional bipolar pacemaker as only two electrical connections are needed for its operation once the implantation procedure with impedance-based depth measurement is complete.

Adapters for Use of the Multi-Electrode Lead with a Conventional Pacemaker

Figure 13:
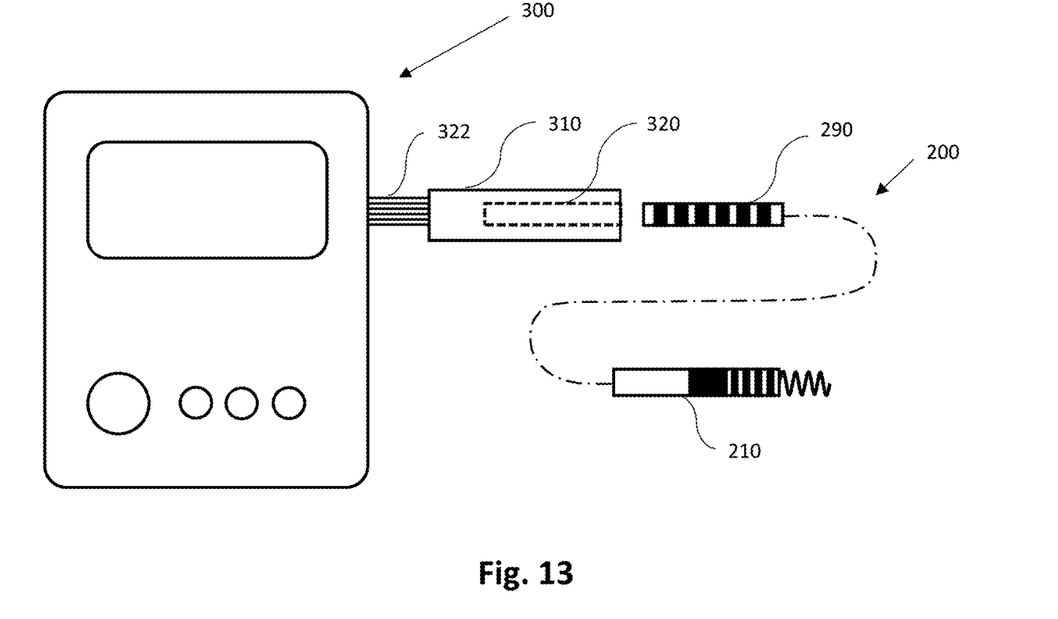
FIG. 13 shows a connection of the multi-electrode lead to a cardiac monitoring and pacing controller during lead implantation procedure.

As described above in greater detail, the use of impedance measurements may be useful in detecting the depth of implantation of the first electrode 220 of the multi-electrode lead 200. To accomplish this purpose, FIG. 13 shows an implantation arrangement of the specialized cardiac monitor and pacing controller 300 and the multi-electrode lead 200 as may be provided for use during the implantation procedure. Although FIG. 13 shows the specialized cardiac monitor 300 as a single unit, in other embodiments, this may be realized as a combination of two or more monitoring and pacing devices, for example one device for monitoring of one or more electrical impedance for a designated set of electrodes, and another device used for temporary pacing.

The specialized cardiac monitor 300 may be equipped with a connector 310 operably connected to the controller of the monitor 300 via a cable 322 containing a sufficient number of wires to independently connect the monitor 300 with each of the individual electrodes of the multi-electrode lead 200. The connector 310 may be equipped with an internal socket receptacle 320 configured to provide electrical connections between the monitor 300 and the plug proximal connector 290 of the multi-electrode lead 200.

In turn, the multi-electrode lead 200 may be equipped with a proximal plug connector 290 featuring individual connections as terminations of the individual conductors leading to corresponding distal electrodes. For example, as seen in FIG. 13, the proximal connector 290 has six connector electrode rings, corresponding to the six electrodes on the distal end 210 of the multi-electrode lead 200, including a first electrode 220, a second electrode 230 and, in this case, four intermediate electrodes located inbetween.

During the implantation procedure, the proximal connector 290 may be inserted into the socket cavity 320 of the connector 310 so as to operably connect the individual distal electrodes to the monitor 300. Implantation of the first distal electrode may then proceed with additional depth control monitoring using electrical impedance as monitored by the monitor 300.

Once the implantation procedure is done, there is a need to operate the multi-electrode lead 200 for a conventional unipolar or bipolar pacing of the heart, such as for example, for pacing of the left bundle branch as discussed above. To address the incompatibility of the proximal connector 290 having more than two electrodes, and to enable the use of a conventional implantable cardiac pacemaker 400, an adapter 500 may be used to connect the multi-electrode (with three electrodes or more) proximal connector 290 to the connector cavity 420 featured in the connection block 410 of a conventional pacemaker 400—see FIG. 14—which typically has only two connectors for a bipolar pacing of the heart.

Figure 14:
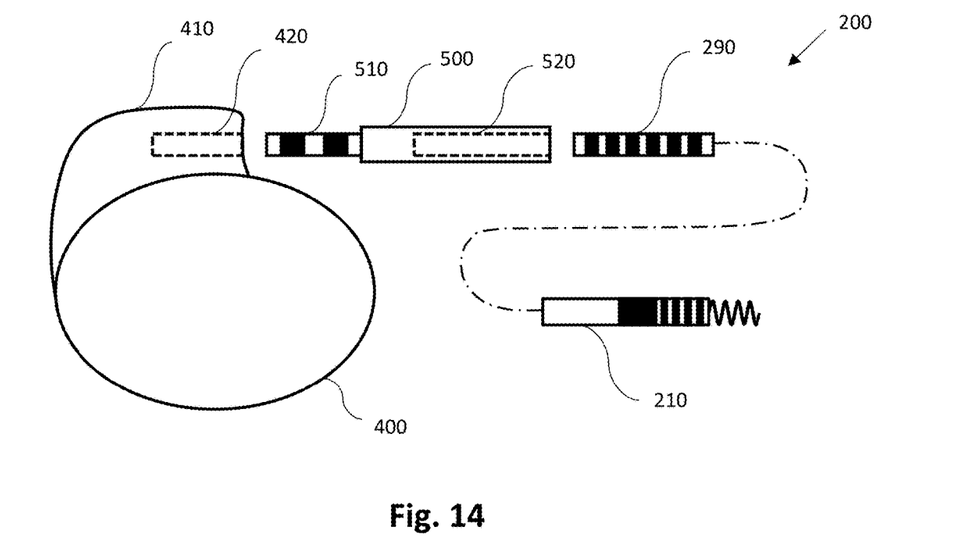
FIG. 14 shows a connection of the multi-electrode lead of the invention to a conventional cardiac pacemaker using a novel adapter of the invention.

The adapter 500 may have a distal end 520 with a socket cavity for accepting the proximal plug connector 290 with more electrical connections (such as three or more) than on the other side of the adapter (typically, two connectors). The socket cavity of the adapter may have the same design as the cavity 320 of the connector 310. On the other side of the adapter 510 there may be a proximal plug connector 510 with only two electrodes, which is made according to the standard convention of a traditional cardiac pacemaker, so as to make it acceptable inside the cavity 420 of the conventional pacemaker 400.

Since the adapter 500 features two proximal electrodes on one end and more than two electrodes on the other end, there is a need for providing corresponding internal electrical connections to bridge one end of the adapter to the other. In one embodiment, the two proximal electrodes of the adapter may be connected to a pair of electrodes at the distal end thereof, which correspond to the first electrode 220 and the second electrode 230. This design is offered to allow abandoning of all of the one or more intermediate electrodes 250 after the implantation procedure as the depth of implantation of the first electrode is determined at the end thereof.

In further embodiments, the adapter 500 may be configured to connect one or more of the intermediate electrodes together and to the first electrode so that the cardiac pacemaker may be operated to provide pacing signals through the first electrode together with one or more additional intermediate electrodes of the multi-electrode lead 200.

In further embodiments, additional configurations of the adapter 500 may be provided. For example, in case a lead failure is detected during the pacing operation, the adapter version connecting the cardiac pacemaker to only the first electrode 220 and the second electrode 230 may be replaced with another version of the adapter in which pacing is applied using one or more of the remaining intermediate electrodes. Since adapter replacement requires only a minor surgery at the subcutaneous pocket location of the implantable cardiac pacemaker, this repair method may be advantageous as compared with replacement of the entire lead to cure the failure of the distal electrode.

In further yet embodiments, the concept of an adapter allowing using of other multi-electrode leads with a conventional bipolar cardiac pacemaker may be extended to allow any desired configuration of active and abandoned distal electrodes to be powered by a limited number of active connectors of a conventional pacemaker. One example of such arrangement may be for using the adapter with a multi-electrode single conduit described in several of my previous patents and patent applications, for example U.S. Pat. No. 10,406,370 and other patents and patent applications of this patent family.

As the final choice of selected electrodes for use in cardiac pacing may only be made at the end of the implantation surgery, a library of various adapters may be provided so as to cover at least some, most frequent, or all of the combinations and permutations of the distal electrodes for a given multi-electrode lead. In this case, a practitioner can decide on the final selection of active electrodes, select the appropriate connector from an available library of connectors, insert the connector to bridge the proximal end of the multi-electrode lead to the conventional pacemaker, and initiate cardiac pacing.

As can be appreciated by those skilled in the art, appropriate markings or indicia may be provided for each of the adapters so as to distinguish them from each other and assure a proper connection between the multi-electrode lead and the cardiac pacemaker.

EXAMPLE

Figure 15:
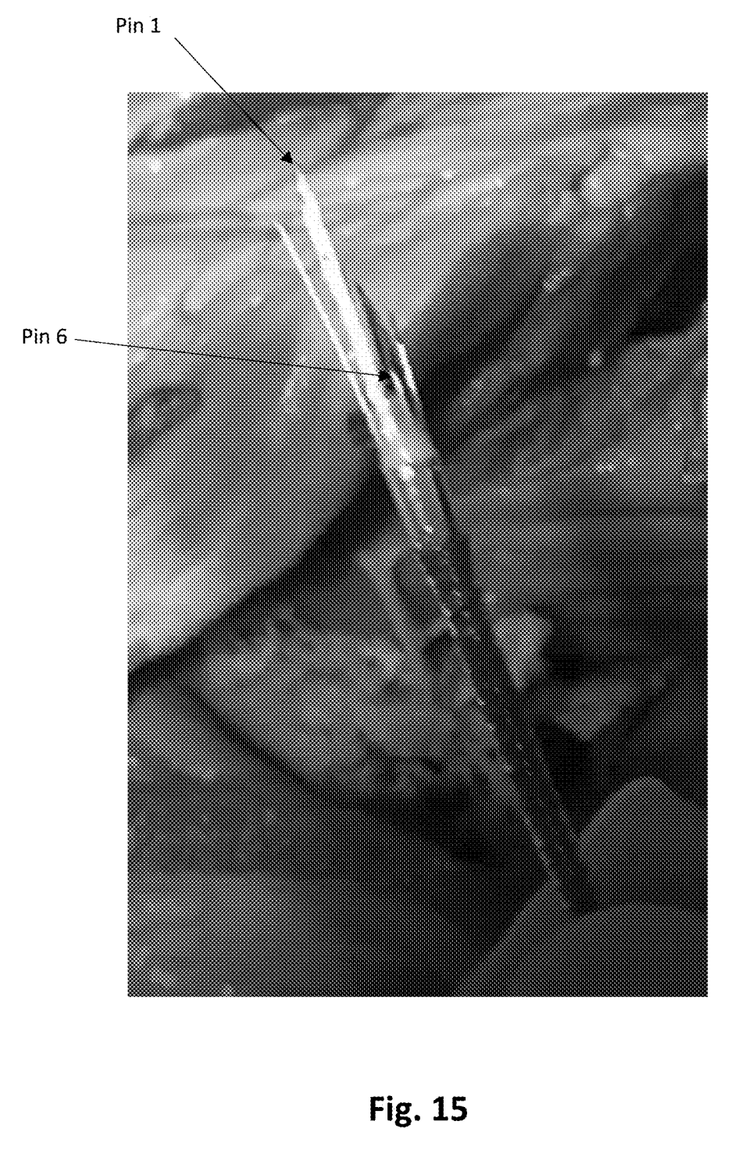
FIG. 15 is a photograph of the test lead produced for an experimental procedure of measuring electrical impedance.

To test the hypothesis that a change in electrical impedance may be used to detect the depth of the distal electrode, a test multi-electrode lead was assembled as a plurality of 6 conductive pins with sharpened distal tips arranged in parallel to each other—with the tips positioned at staggered depths of about 2 mm apart—see FIG. 15.

A freshly diseased non-beating porcine heart was used for the experiment. Unipolar impedance was measured for each of the pins while test impulses were sent by a dedicated cardiac stimulator with a 4V amplitude at 60 beats per minute. Each impulse was sent for 0.1 seconds.

The test lead was gradually inserted into the wall of the heart. Impedance for each pin was measured at 5 insertion depths. Results of the measurements are presented below in Table 1.

TABLE 1

Unipolar impedance measurements (Ohm) for various progressive penetration depths

|  | Depth 1 | Depth 2 | Depth 3 | Depth 4 | Depth 5 |
| --- | --- | --- | --- | --- | --- |
| Distal pin 1 (longest) | 410 | 320 | 300 | 250 | 290 |
| Pin 2 | 400 | 330 | 310 | 280 | 310 |
| Pin 3 | 420 | 361 | 320 | 290 | 325 |
| Pin 4 | 600 | 400 | 430 | 330 | 370 |
| Pin 5 | Open | 750 | 370 | 340 | 450 |
| Proximal pin 6 (shortest) | Open | 1500 | 600 | 406 | 556 |

"Open" measurement denotes no electrical contact of the corresponding pin with the cardiac tissue at depth 1.

As can be seen from the table, unipolar impedance measurements initially went down as the depth of penetration increased. At some point, as the tip of each pin approached went deeper into the cardiac muscle, the impedance went up again indicating entering a risk area for penetration into the left ventricular cavity. In this particular test condition, a change of impedance of about 50 Ohms may be sufficient to detect the depth of the first electrode.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for electrode implantation at a desired depth and pacing of a heart using thereof, the method comprising the following steps:
   a. providing a multi-electrode lead, the multi-electrode lead in turn comprising:
      i. a flexible elongated insulated body with a distal portion,
      ii. a first electrode extending distally from the distal portion of the insulated body of the multi-electrode lead,
      iii. a second electrode proximally spaced along the distal portion of the insulated body from the first electrode, and
      iv. an intermediate electrode located on the insulated body of the multi-electrode lead between the first electrode and the second electrode, wherein the intermediate electrode is spaced from the first electrode by a predetermined distance corresponding to the desired depth of electrode implantation into cardiac tissue,
   b. positioning the distal portion of the multi-electrode lead in the heart adjacent to a desired location of implantation of the first electrode;
   c. initiating monitoring of electrical impedance of the intermediate electrode;
   d. detecting a baseline electrical impedance thereof while located in a blood stream inside the heart;
   e. initiating implantation deployment of the first electrode into cardiac tissue while continuing to monitor electrical impedance of the intermediate electrode;
   f. upon detecting a change in electrical impedance of the intermediate electrode at or exceeding a predetermined electrical impedance change threshold, ceasing further deployment of the first electrode as reaching the desired implantation depth; and
   g. initiating a bipolar pacing of the heart using the first electrode and the second electrode.

2. The method as in claim 1, wherein said desired location of implantation for the first electrode is an interventricular septum approached from a right ventricle of the heart, whereby said step (f) is performed for pacing of the left bundle branch of the heart.

3. The method as in claim 1, wherein said electrical impedance is measured between said intermediate electrode and a ground electrode.

4. The method as in claim 1, wherein said electrical impedance is measured between said intermediate electrode and the first electrode.

5. The method as in claim 1, wherein said predetermined electrical impedance change threshold is at least 20 percent of said electrical impedance baseline measurement value.

6. The method as in claim 1, wherein the step (f) further comprising a step of verifying said intermediate electrode being in contact with the cardiac tissue by confirming pacing capture of the heart using the intermediate electrode.

7. The method as in claim 1, wherein the multi-electrode lead of step (a) further comprising additional intermediate electrodes forming together with the intermediate electrode a plurality of spaced apart intermediate electrodes located between the first electrode and the second electrode, wherein step (c) of the method further comprising selecting an intermediate electrode corresponding to the desired depth of implantation and monitoring electrical impedance therefore, whereby in step (f) the first electrode is deployed at a desired depth detected using electrical impedance measurements of the selected intermediate electrode.

8. The multi-electrode lead for use with the method of claim 7, wherein at least some electrodes of the plurality of intermediate electrodes are rings spaced apart between the first electrode and the second electrode.

9. The multi-electrode lead as in claim 8, wherein the one or more intermediate electrodes are mounted on a removable sheath surrounding the elongated body, wherein the sheath is configured for removal from the elongated body once the implantation procedure is complete.

10. The multi-electrode lead as in claim 8, wherein at least some electrodes of the plurality of intermediate electrodes are parallel conductive strips with electrically exposed tips spaced apart between the first electrode and the second electrode.

11. The multi-electrode lead as in claim 10, wherein the conductive strips extend to the distal end of the distal portion of the insulated body, the electrically exposed tips of the at least some electrodes of the plurality of intermediate electrodes are formed by a dissolvable coating applied at the distal end of the multi-electrode lead.

12. The method as in claim 1, wherein steps (c) through (f) are performed with a specialized cardiac monitor configured for detection of electrical impedance of electrodes suitable for cardiac pacing, and step (g) is performed using a conventional cardiac pacemaker.

13. The method as in claim 12, wherein said multi-electrode lead of step (a) has a proximal portion equipped with three or more connector electrodes operatively connected to corresponding electrodes on the distal portion thereof.

14. The method as in claim 13, wherein the step (f) further comprising using an adapter to operatively connect the conventional cardiac pacemaker to the first electrode and the second electrode.

15. The method as in claim 14, wherein the adapter further comprises a distal end and a proximal end, the distal end is configured for attachment and electrical coupling to a greater number of electrodes on the proximal portion of the multi-electrode lead than the number of electrodes on the proximal end of the adapter configured to be electrically coupled to the conventional pacemaker.

16. The method as in claim 14, wherein the adapter further comprises a distal end with a socket cavity with at least three electrodes configured for connecting to the proximal portion of the multi-electrode lead, the adapter further comprises a plug proximal end with two electrodes configured for connecting to the conventional pacemaker.

17. The method as in claim 1, wherein electrical impedance measurements in steps (c) through (f) are synchronized with a natural heart rhythm.

\* \* \* \* \*